(12) United States Patent
Crownie

(10) Patent No.: US 11,083,638 B2
(45) Date of Patent: Aug. 10, 2021

(54) CROWN BOTTOMS: DISPOSABLE UNDERGARMENTS

(71) Applicant: Naomie Crownie, Stone Mountain, GA (US)

(72) Inventor: Naomie Crownie, Stone Mountain, GA (US)

( * ) Notice: Subject to any disclaimer, the term of this patent is extended or adjusted under 35 U.S.C. 154(b) by 708 days.

(21) Appl. No.: 15/696,248

(22) Filed: Sep. 6, 2017

(65) Prior Publication Data
US 2019/0070046 A1    Mar. 7, 2019

(51) Int. Cl.
| | |
|---|---|
| A61F 13/496 | (2006.01) |
| A61F 13/84 | (2006.01) |
| A41B 9/00 | (2006.01) |
| A61F 13/56 | (2006.01) |
| A61F 13/511 | (2006.01) |
| A61F 13/514 | (2006.01) |
| A61F 13/53 | (2006.01) |
| A61F 13/505 | (2006.01) |
| A61F 13/49 | (2006.01) |

(52) U.S. Cl.
CPC ............ *A61F 13/496* (2013.01); *A41B 9/001* (2013.01); *A41B 9/008* (2013.01); *A61F 13/505* (2013.01); *A61F 13/511* (2013.01); *A61F 13/51458* (2013.01); *A61F 13/53* (2013.01); *A61F 13/5655* (2013.01); *A61F 13/8405* (2013.01); *A41B 2400/22* (2013.01); *A41B 2400/36* (2013.01); *A41B 2400/52* (2013.01); *A61F 2013/49092* (2013.01); *A61F 2013/5055* (2013.01); *A61F 2013/530131* (2013.01); *A61F 2013/8408* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 5,024,667 | A | * | 6/1991 | Malcolm | ............... A61L 15/585 428/198 |
| 5,037,411 | A | * | 8/1991 | Malcolm | ................ C09J 153/02 604/358 |
| 5,057,571 | A | * | 10/1991 | Malcolm | ............... A61L 15/585 524/505 |
| 5,139,687 | A | * | 8/1992 | Borgher, Sr. | .......... C11D 3/001 510/101 |
| 5,246,611 | A | * | 9/1993 | Trinh | ....................... A61K 8/39 510/515 |
| 5,384,186 | A | * | 1/1995 | Trinh | ........................ C08L 5/16 349/123 |
| 5,849,816 | A | * | 12/1998 | Suskind | ................ C08F 251/00 523/201 |

(Continued)

*Primary Examiner* — Guy K Townsend
(74) *Attorney, Agent, or Firm* — Ronald D. Baker; Baker & Co. Law Group, LLC.

(57) ABSTRACT

The present invention is a disposable garment for alleviating unpleasant scents and bodily waste when worn by users. Disposable undergarments such as diapers and other similar garments can be a challenge to use when the garment has been soiled. Various applications of specially designed layers of material can be an effective tool when odors and excretion are unbearable. Garments that are manufactured to combat the difficult process of dealing with bodily waste is a benefit to the public; especially when excretion occurs unexpectedly.

5 Claims, 2 Drawing Sheets

(56) References Cited

U.S. PATENT DOCUMENTS

| | | | | |
|---|---|---|---|---|
| 6,575,952 B2* | 6/2003 | Kirk | | A61F 13/53418 604/378 |
| 6,645,190 B1* | 11/2003 | Olson | | A61F 13/581 604/389 |
| 7,919,666 B2* | 4/2011 | Odorzynski | | A61F 15/001 604/359 |
| 7,977,530 B2* | 7/2011 | Dodge, II | | A61F 13/535 604/367 |
| 7,977,531 B2* | 7/2011 | Dodge, II | | B01J 20/103 604/367 |
| 9,474,661 B2* | 10/2016 | Fouillet | | A61F 13/00051 604/367 |
| 2001/0003797 A1* | 6/2001 | Guevara | | C08L 23/02 604/364 |
| 2001/0031938 A1* | 10/2001 | DeLucia | | A61K 8/738 602/45 |
| 2002/0034913 A1* | 3/2002 | Curro | | B32B 38/0012 442/381 |
| 2002/0039867 A1* | 4/2002 | Curro | | B29C 66/45 442/373 |
| 2003/0092813 A1* | 5/2003 | Blenke | | C09J 123/10 524/425 |
| 2003/0114806 A1* | 6/2003 | La Fortune | | A61F 13/8405 604/359 |
| 2003/0135172 A1* | 7/2003 | Whitmore | | A61L 15/60 604/359 |
| 2003/0191210 A1* | 10/2003 | Autran | | C08L 67/04 523/105 |
| 2004/0127866 A1* | 7/2004 | Odorzynski | | A61F 13/8405 604/359 |
| 2005/0014891 A1* | 1/2005 | Quinn | | B32B 27/325 524/556 |
| 2005/0101927 A1* | 5/2005 | Joseph | | A61L 15/50 604/367 |
| 2005/0112085 A1* | 5/2005 | MacDonald | | B01J 20/08 424/76.1 |
| 2006/0025731 A1* | 2/2006 | Cohen | | A61L 15/20 604/359 |
| 2006/0205873 A1* | 9/2006 | Wood | | C08B 37/0012 525/70 |
| 2007/0264520 A1* | 11/2007 | Wood | | B32B 5/02 428/606 |
| 2008/0200890 A1* | 8/2008 | Wood | | A61L 15/26 604/360 |
| 2008/0221546 A1* | 9/2008 | Quinn | | C09J 123/0853 604/389 |
| 2008/0300561 A1* | 12/2008 | Stridfeldt | | A61L 15/44 604/367 |
| 2009/0024101 A1* | 1/2009 | Toshishige | | A61F 13/8405 604/359 |
| 2009/0134049 A1* | 5/2009 | Melik | | A61F 13/4902 206/370 |
| 2009/0192481 A1* | 7/2009 | Dodge, II | | A61L 15/18 604/372 |
| 2009/0192482 A1* | 7/2009 | Dodge, II | | A61F 13/53752 604/385.23 |
| 2013/0165880 A1* | 6/2013 | Amos | | A61F 13/8405 604/367 |
| 2015/0209200 A1* | 7/2015 | Fouillet | | A61L 15/60 604/369 |
| 2015/0209468 A1* | 7/2015 | Aviles | | A61K 9/7007 424/402 |
| 2016/0051423 A1* | 2/2016 | Ota | | A61L 15/46 604/359 |
| 2017/0266056 A1* | 9/2017 | Eimann | | A61F 13/15723 604/367 |
| 2017/0266057 A1* | 9/2017 | Eimann | | B23K 26/0006 604/367 |
| 2017/0266941 A1* | 9/2017 | Eimann | | A61F 13/49 604/367 |
| 2019/0070046 A1* | 3/2019 | Crownie | | A61F 13/8405 604/367 |

* cited by examiner

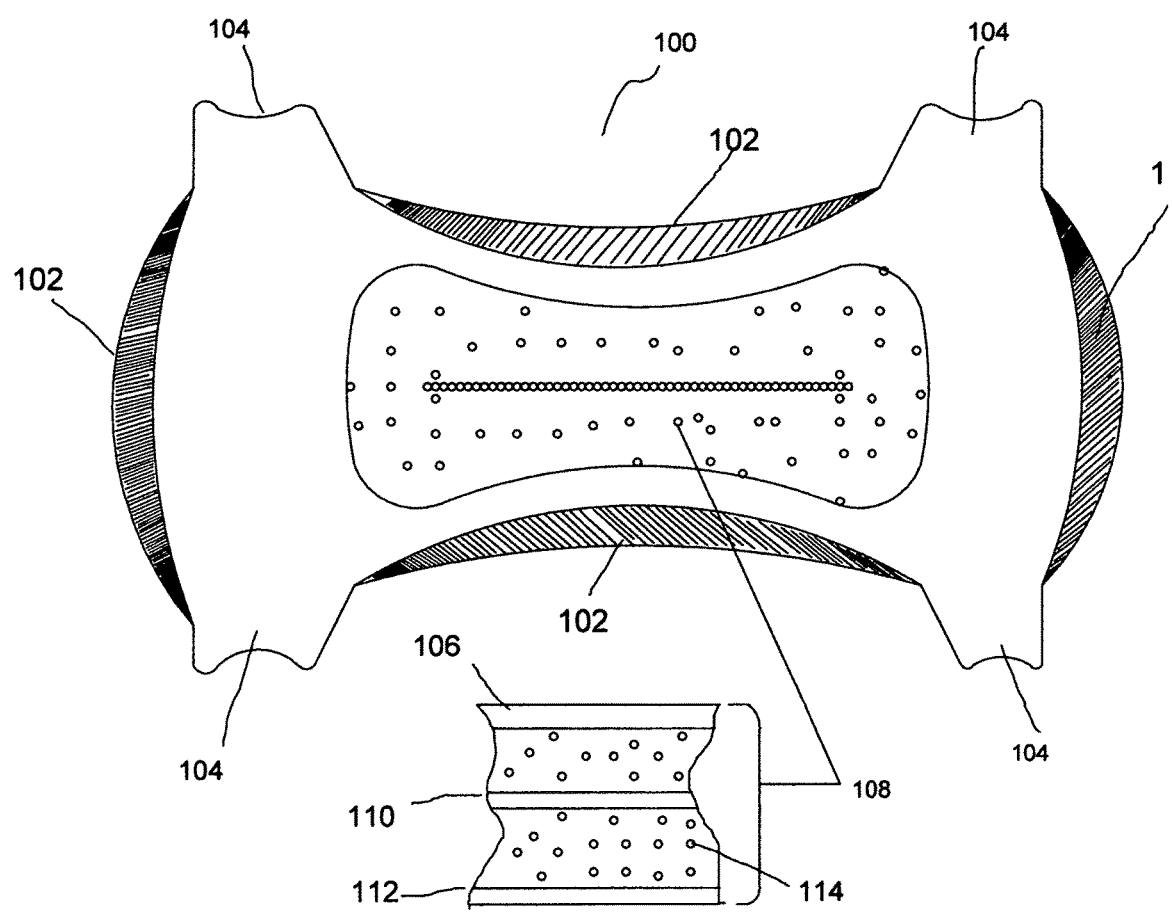

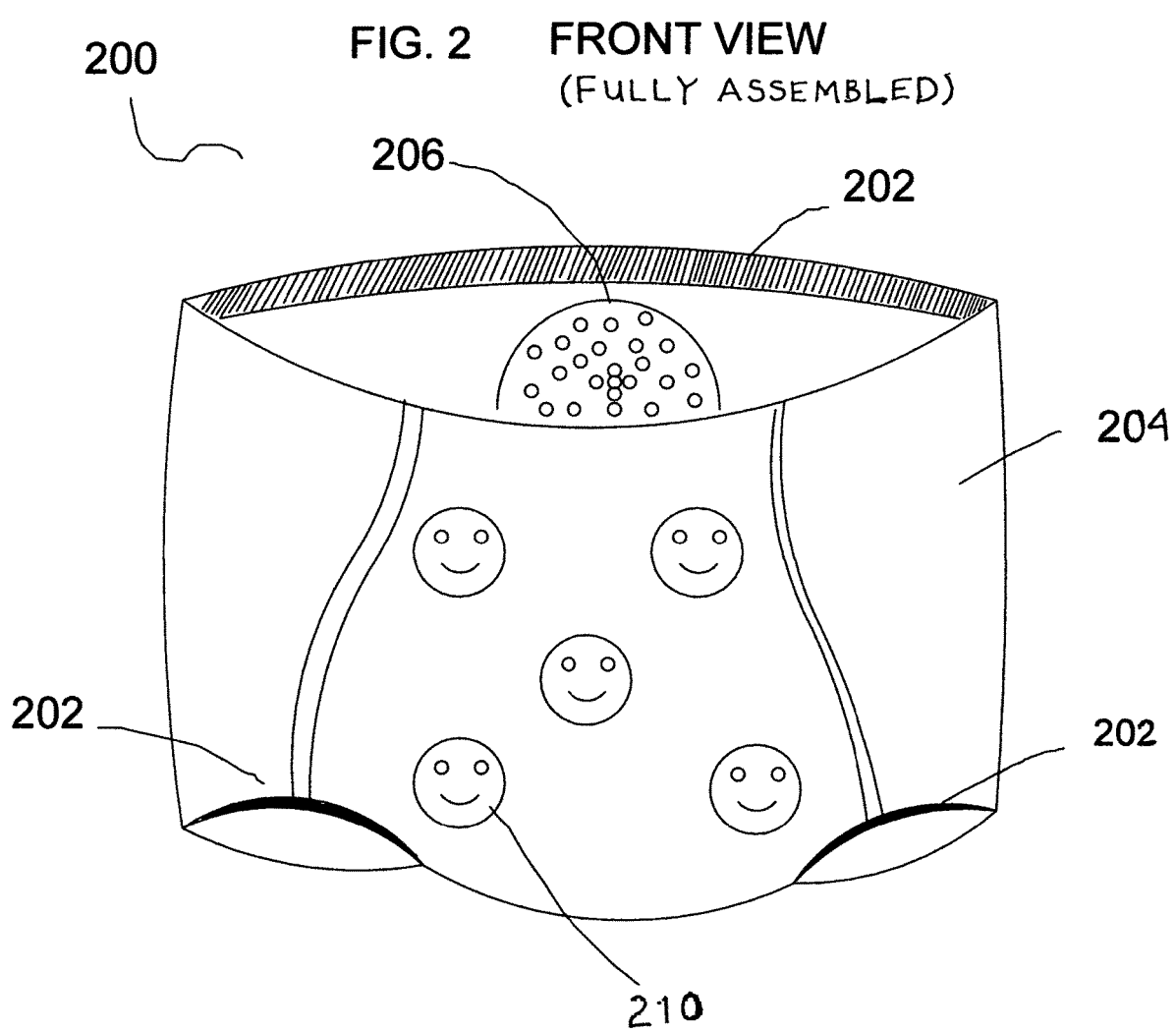

CROWN BOTTOMS: DISPOSABLE UNDERGARMENTS

The present application claims priority to the earlier filed provisional application having Ser. No. 62/383,744, and hereby incorporates subject matter of the provisional application in its entirety.

FIELD OF INVENTION

The subject disclosure relates to a system for combating offensive odors. More particularly, the present disclosure relates to a system and method of combating such odors by using a series of embodiments.

COPYRIGHT AND TRADEMARK NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever. Trademarks are the property of their respective owners.

BACKGROUND

Traditionally, disposable undergarments are considered items of clothing worn beneath other apparel that is often used to keep outer clothing from being soiled by body excretion in the event individuals are in the process of excreting waste from their bodies. Customarily, disposable undergarments have been inconvenient and an unhygienic ordeal for those charged with the task of changing and disposing of conventional garments. Not only have those charged with changing disposable undergarments had to avoid being soiled by excretion but also had to endure offensive odors in the process.

Users have dealt with traditional garments such as diapers but are eager to embrace enhancements to the conventional brand of disposable garments in the marketplace. Although the use of disposable garments is necessary, it is an inconvenience for the public due to the challenge of accomplishing the job of changing those who wear such garments without soiling themselves or the immediate surroundings, not to mention dealing with offensive odors.

BRIEF SUMMARY

The proposed invention is an incontinence device as outlined which allows users to benefit from a broader range of improvements to combat offensive odors and make changing disposable garments bearable. Using a broader range of multi-tiered barriers such as the ability to absorb odors and release pleasant scents during the removal of the undergarment will greatly enhance the current task of changing soiled garments.

BRIEF DESCRIPTION OF THE DRAWINGS

Certain illustrative embodiments illustrating objects and advantages may be best understood by reference detailed description that follows taken in conjunction with the accompanying drawings in which:

FIG. 1 is a diagram of a top-view of the proposed invention consistent with certain embodiments of the present invention.

FIG. 2 is a diagram of a front-view consistent with certain embodiments of the present invention.

DETAILED DESCRIPTION

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one, or more than one. The term "plurality", as used herein, is defined as two, or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an exemplary embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

Reference throughout this document to "scent pellets" or similar terms refers to a small compressed particle for repelling odors that transmit scents to the surface of the garment. Thus, the appearance of similar phrases throughout this specification may not be limited to just the term "scent pellets" but when the description refers to a means of releasing pleasant scents then it may be inferred that the description refers to scent pellets.

Reference throughout this document to "layer" refers to the portions of the garment that make up the inner and outer wall of the disposable garment. Furthermore, the particular features, structures, or characteristics may be combined in any suitable manner in one or more embodiments without limitations.

Reference throughout this document to attachment straps refers to any method of securing the garment to a person's body such as adhesive but is not limited to this example. Therefore, where ever this specification refers to any means of attachment it will not be limited to any specific means of attachment but rather any number of attachment methods may be combined to create an attachment strap for purposes of the present embodiment.

The material that a disposable garment is made of is an essential aspect to the garment because it determines the quality of the garment and often dictates a user's experience. From a convenience perspective, the aspects of the garment which affects the user's sensory factors are an important attribute for effectively presenting a more inviting garment. In common use of disposable garments, most manufacturers use a deodorizer which is applied to various external surfaces of the garment to minimize the offensive scents of the garment. In a non-limiting example, because odors emit from surfaces of garments then a combination of structures and special liners must be used to deal with odors and release scents that are pleasant to the user. Conventional garments merely attempt to mask the odor by applying more deodorizers in hopes that the deodorizer will over power the offensive odors.

Using a combination of various features and substances such as scent pellets and liners, provides an effective method of helping to eliminate odors and ensuring a pleasant experience of changing disposable garments. In a non-limiting example, when the defecating scent is released against the liner of the garment the odor passes through the soft dry weave liner to filler material embedded with scent pellets which simultaneously releases a pleasant scent to help eliminate odors.

In an exemplary embodiment, the use of scent pellets and absorbent pad liners that help control odors in a manner that manufacturers have not previously been able to accomplish is an inventive aspect that will greatly improve the ordeal of changing disposable garments. A challenge to manufacturers is how to effectively control not only the odors but also the moisture and other waste that is associated to the odor. Eliminating the odors at the origination point is a critical aspect of the current embodiment. In the event of bodily excretion, crown bottoms create a controlled environment for all involved.

In the exemplary embodiment, the current invention consists of elastic leg and waist band seals that make up the disposable garment which helps to ensure a sealed and isolated environment to prevent any waste from escaping the compartment between a persona's skin and the liner of the garment. A special composite allows air to flow through a dry weave surface. Once the excretion comes in contact with the composite material air is allowed to flow through the material to help eliminate moister. In a non-limiting example, the invention has hypoallergenic fragrances which may include vanilla, cherry, lavender, strawberry, Jasmine, orchard, and baby powder.

In an additional embodiment, the Crown Bottom system also includes a variety of bands along the waist and legs as well as, by example, side Velcro® attachments and bands that prevents leakage. The Crown Bottom system uses a special elastic material that fully fits along the curves of the user's legs by contouring to a user's skin to create a seal which prevents both odors and any excess wetness from escaping. The various elastic bands and attachments conceal the odors by a method that allows for greater effectiveness of released scents by the pellets which serve to combat the environmental odors immediately around the disposable garment. The scent that is released creates a pleasant atmosphere for not only those who are in direct contact with the disposable garments but the public in general.

In an exemplary embodiment, the current embodiment incorporates a three-layer system that effectively deals with the effort of eliminating odors. First, the crown bottom system includes a super soft inner panel that is in constant contact with the user's skin that allows air to flow through the dry weave surface. This is important to allow the odors and wetness to easily flow across the barriers of multi-tiered system. Secondly, the system also includes an absorbent middle layer that consists of pad liner, filler material, and scent pellets evenly distributed that releases a pleasant odor. The middle layer is the most critical layer with regard to the control of odors because this is the area of the garment control wetness and release scents as a result of contact by human fluid which may flow across the surface of the pad liners and scent pellets. Third, the system includes a water proof laminated outer surface that in a non-limiting example may be made out of non-woven material which incorporates an appealing design. This outer surface helps prevent any excretion from leaving the garment mainly through the surface of the disposable garment which could be a significant inconvenience for the public.

Turning now to FIG. 1, this figure presents a top-view and a cross-sectional view of the disposable garment for an exemplary diagram of the garment consistent with certain embodiments of the present invention. A disposable garment 100, that may be worn by the use of an attachment apparatus 104 which secures the garment to the user. The disposable garment 100 includes elastic bands 102 along the user's waist and thigh areas to prevent leakage. When the garment 100 is securely fitted, the absorbent pad layers 200 serves various purposes due to the multi-tiered system which helps to defend against wetness and odors. The inner layer 106 serves as a transient layer that allows air to flow through the dry weave pattern of the disposable garment. This weave pattern is critical because it maintains dryness while dealing with wetness by allowing fluids to pass through the specially made weave patterns of the garment which allows the user to still experience comfort while simultaneously transferring wetness to the inner layers of the garment. The combination of the layers 108 of the garment provides for a three-layer system that include, filler material, absorbent pad liners, and scent pellets which releases a pleasant odor for the user by utilizing a multi-tiered barrier. The absorbent layer 110 is a critical feature of the multi-tiered system in that it is the layer that releases scents upon contact with odors. The outer impermeable panel 112 is water proof yet made out of material that provides a moisture barrier that prevents wetness from escaping the garment while being worn. The absorbent pad liners 106 are sandwiched by filler material 114 that encompasses the pad liner from all sides.

Turning now to FIG. 2, this figure presents a side-view of the disposable garment for an exemplary diagram of the garment consistent with certain embodiments of the present invention. The schematic illustrates a fully assembled disposable garment 200, that demonstrates how the garment fits the user once all attachments 204 are secured. The disposable garment 200 includes elastic bands 202 along the user's waist and thigh areas to prevent leakage. When the garment 200 is securely fitted, the absorbent pad liners serves various purposes due to the multi-tiered system 206 to include filler material, absorbent pad liners, and scent pellets which helps to defend against wetness and odors. The elastic bands 202 prevents leakage and seals odors once properly secured to the user's body. Upon securing the garment the multi-tiered system 206 firmly fits against the user's buttocks and front portion near the user's genitals to help defend against unpleasant odors by use of the multi-tiered system if the garment is soiled. The garment includes various cosmetic designs 210 to provide an appealing appearance. In a non-limiting example, the disposable garment may exhibit depictions of smiling faces or floral designs.

I claim:

1. A method for blocking offensive odors in disposable garments using a multi-tiered system; comprising the steps of:
    (a) absorbing urine and other human excretion through an inner panel surface of said disposable garment;
    (b) allowing excrement to flow into a filler material;
    (c) allowing excrement to make contact with a plurality of scent pellets;

(d) releasing a pleasant scent through a reactive agent on the surface of the scent pellets upon contact with the surface of the scent pellets;

(e) transferring excrement through a plurality of pad liners that is impregnated with a pleasant perfume to accentuate scents created by the scent pellets;

(f) capturing the remaining excrement within the disposable garment once the excrement has flowed to an outer laminated panel and not allowed to further penetrate the outer laminated panel of the disposable garment, wherein the scent pellets are evenly distributed throughout the filler material, wherein the filler material is embedded with the scent pellets to simultaneously release a pleasant scent to eliminate odors; and (g) preventing, by the elastic leg and waist band seals, the excrement from escaping a compartment between a persona's skin and the pad liners of the disposable garment.

2. The method for blocking offensive odors in said disposable garments according to claim 1, wherein step (a) further comprises absorbing urine and other human excretion through the inner panel surface of said disposable garments in order to contain odors.

3. The method for blocking offensive odors in said disposable garments according to claim 1, wherein step (c) further comprises the scent pellets releasing a moisture-activated agent.

4. The method for blocking offensive odors in said disposable garments according to claim 1, wherein step (d) further comprises transferring the urine and other human excrements through a plurality of pad liners that will absorb an abundant amount of urine and release an agent that will accentuate a scent released by the scent pellets.

5. The method for blocking offensive odors in disposable garments according to claim 1, wherein step (e) further comprises a multi-tiered reaction that releases reactive agents from step (c) and step (e) in a manner that allows a release agent to activate through contact by both the scent pellets and subsequently absorbent pad liners; wherein release allows for a dual combat of odors that will significantly eliminate odors.

* * * * *